United States Patent [19]
Suzuki et al.

[11] Patent Number: 6,015,796
[45] Date of Patent: Jan. 18, 2000

[54] METHOD FOR TREATING AIDS

[75] Inventors: Fujio Suzuki; Hidetaka Sasaki; Makiko Kobayashi, all of Galveston, Tex.

[73] Assignees: Zeria Pharmaceutical Co., Ltd.; Natsu Maruyama, both of Tokyo, Japan

[21] Appl. No.: 09/038,041

[22] Filed: Mar. 11, 1998

[51] Int. Cl.$^7$ ..................................................... A61K 31/70
[52] U.S. Cl. ................................ 514/45; 514/49; 514/50; 514/269; 514/54; 536/1.1; 536/22.1; 536/124; 435/101; 435/134; 424/92
[58] Field of Search ................................. 536/1.1, 22.1, 536/124; 435/101, 134; 424/92, 45; 514/45, 49, 50, 54, 269

[56] References Cited

U.S. PATENT DOCUMENTS

| | | | |
|---|---|---|---|
| 4,746,511 | 5/1988 | Kobatake et al. | 424/92 |
| 5,521,161 | 5/1996 | Malley et al. | 514/45 |

FOREIGN PATENT DOCUMENTS 9520673  8/1995  France .

OTHER PUBLICATIONS

Arp et al., "Expression and Immunogenicity of the Entire Human T Cell Leukemia Virus Type I Envelope Protein Produced in a Baculovirus System", *Journal of General Virology*, 74(2), 211–222 (1993).

Okunade et al., "Antimicrobial Properties of Alkaloids from *Xanthorhize Simplicissima*," *Journal of Pharmaceutical Sciences*, 83(2), 404–406 (Mar. 1994).

Guleria et al., "Auxotropic Vaccines for Tuberculosis," *Nature Medicine (New York)*, 2(3), 334–337 (1996).

Ishihara et al., "Phase II Clinical Trial of MY–1 for Adult T Cell Leukemia," *Skin Cancer*, 10(2), 257–270 (1995); only Abstract provided.

Bernier et al., "Mycobacterium Tuberculosis Mannose–Capped Lipoarabinomannan Can Induce NR–kappaB–Dependent Activation of Human Immunodeficiency Virus Type 1 Long Terminal Repeat in T Cells," *J. General Virology*, 79(pt. 6), 1353–1361 (Jun., 1998).

"Diagnostics—*Mycobacterium Avium*," *AIDS Weekly*, Issue of Nov. 28, 1994, only 349 word abstract provided, page location(s) not available.

Vila et al., "Absence of Viral Rebound After Treatment of HIV–Infected Patients with Didanosine and Hydroxycarbamide," *The Lancet*, 350, 635–636 (Aug. 30, 1997).

Yoshiro Hayashi, et al., Biotherapy, vol. 7, pp. 63–69, "The Effect of Combination Therapy of Radiation and Z–100, and Arabinomannan on Tumor Growth in Mice", 1994.

Hideki Ohnota, et al., Antimicrobial Agents and Chemotherapy, vol. 34, No. 4, pp. 605–609, "3–Azido–3'–Deoxythymidine Prevents Induction of Murine Acquired Immunodeficiency Syndrome in C57BL/10 Mice Infected with LP–BM5 Murine Leukemia Viruses, A Possible Animal Model for Antiretroviral Drug Screening", Apr. 1990.

Osamu Ohya, et al, The Clinical Report, vol. 24 No 4, pp. 441–448, "Hematopoietic Effect of Z–100, An Extract From Human Type Tubercle Bacilli (2)—Therapeutic Effect on the Hematological and Immunological Damage in X–Ray Irradiated Mice", (with English Summary) (Mar. 1990).

M. Kobayashi, et al., The 1995 UCLA/UCI AIDS Symposium, p. 40, "Mechanisms of HIV Disease", Mar. 2–5, 1995, Palm Springs, CA, Hyatt Regency Suites.

*Primary Examiner*—L. Eric Crane
*Attorney, Agent, or Firm*—Oblon, Spivak, McClelland, Maier & Neustadt, P.C.

[57] ABSTRACT

The present invention relates to a method for treating AIDS, which comprises administering to an HIV-infected patient (a) a composition containing as the primary component a polysaccharide derived from a hot water extract of human-type tubercle bacillus and (b) a nucleoside-type anti-HIV agent. Due to the incorporation of composition (a), the present invention enhances the therapeutic effect of nucleoside-type anti-HIV agents on AIDS.

19 Claims, 1 Drawing Sheet

METHOD FOR TREATING AIDS

BACKGROUND OF THE INVENTION

1. Field of the Invention

The present invention relates to a method for treating AIDS (Acquired Immunodeficiency Syndrome).

2. Background Art

AIDS is a disease caused by HIV (Human Immunodeficiency Virus) infection, and the number of patients suffering AIDS has markedly increased in recent years. In therapy for AIDS, there have been used nucleoside-type anti-HIV agents such as Zidovudine (Azidothymidine, AZT) and Didanosine (ddI).

However, these conventional anti-HIV agents do not provide sufficient therapeutic effect and thus development of new AIDS therapeutic means is demanded.

SUMMARY OF THE INVENTION

The present inventors have conducted careful studies in an attempt to improve the therapeutic effect of nucleoside-type anti-HIV agents on AIDS patients. They have found that the combined use of a hot water extract of human-type tubercle bacillus and a nucleoside-type anti-HIV agent dramatically improves the mortality of AIDS patients as compared with the case in which the anti-HIV agent alone is administered, leading to completion of the invention. The hot water extract of human-type tubercle bacillus is known as an agent which is effective for ameliorating reduced white blood cell count stemming from radiotherapy.

Accordingly, the present invention provides a method for treating AIDS, which comprises administering to an HIV-infected patient (a) a composition containing as the primary component a polysaccharide derived from a hot water extract of human-type tubercle bacillus and (b) a nucleoside-type anti-HIV agent.

The present invention also provides a remedy for AIDS which comprises as active ingredients (a) a composition containing as the primary component a polysaccharide derived from a hot water extract of human-type tubercle bacillus and (b) a nucleoside-type anti-HIV agent.

The present invention further provides an enhancer drug which comprises as an active ingredient (a) a composition containing as the primary component a polysaccharide derived from a hot water extract of human-type tubercle bacillus and which improves therapeutic effect of a nucleoside-type anti-HIV agent on AIDS patients.

The present invention further provides use, as an enhancer drug for improving therapeutic effect of a nucleoside-type anti-HIV agent on AIDS patients, of (a) a composition containing as the primary component a polysaccharide derived from a hot water extract of human-type tubercle bacillus.

The present invention still further provides use, for the manufacture of a remedy for AIDS, of (a) a composition containing as the primary ingredient a polysaccharide derived from a hot water extract of human-type tubercle bacillus and (b) a nucleoside-type anti-HIV agent.

These and other objects, features, and advantages of the present invention will become apparent from the following description.

BEST MODE FOR CARRYING OUT THE INVENTION

Figure 1:
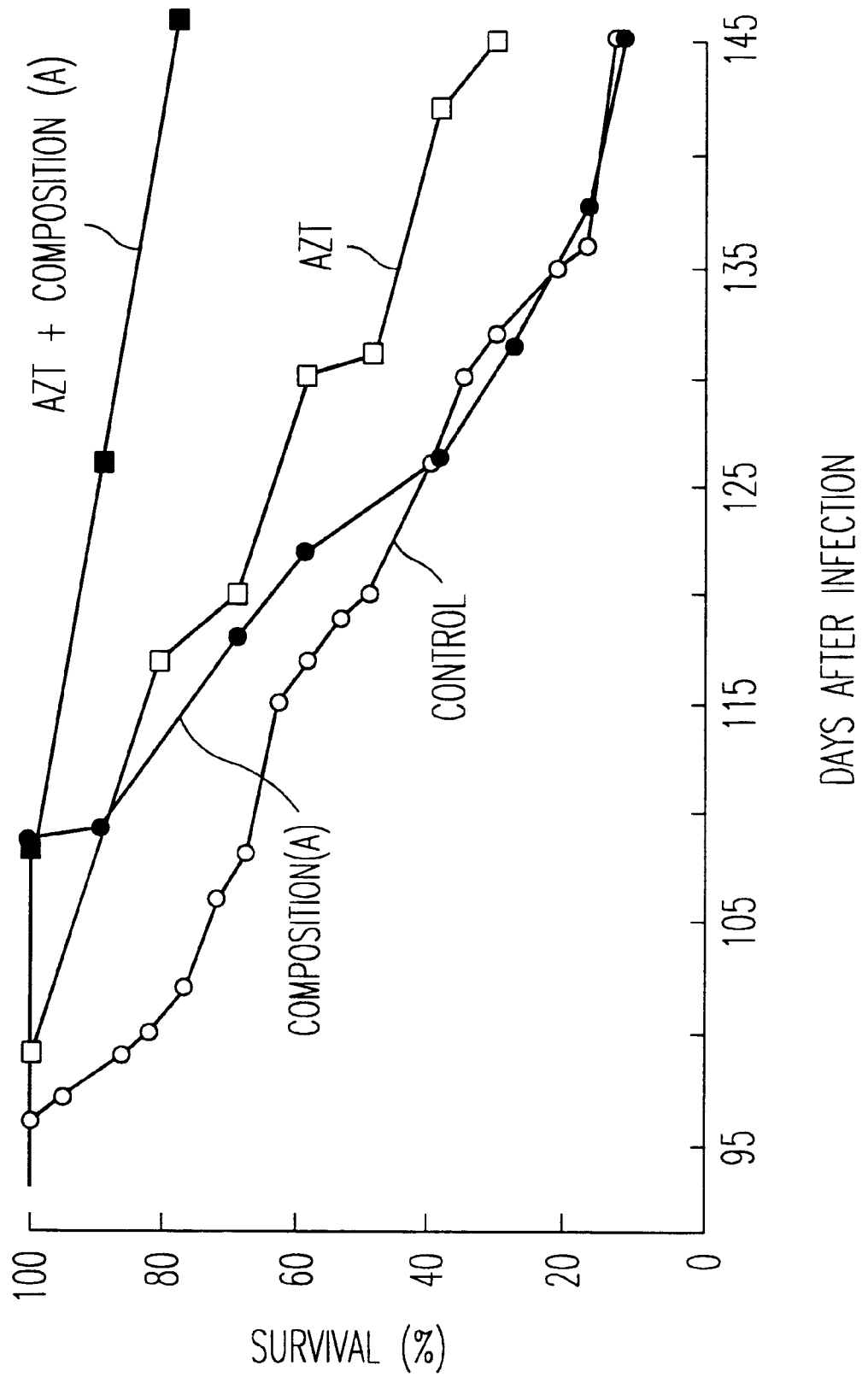
FIG. 1 is a graph showing the chronological change of the survival rate of mice suffering murine AIDS (MAIDS).

The composition (a); i.e., a composition containing as the primary component a polysaccharide derived from a hot water extract of human-type tubercle bacillus, which is used in the present invention is known to have excellent recovery action against reduction of white blood cells caused by radiotherapy for cancers (see among others "The Clinical Report (Basic and Clinical Report)," 24(4), 1973 (1990) and "Nippon Igaku Hoshasen Gakkai Zasshi," 50(8), 993 (1990)).

However, the effect of this composition (a) on AIDS is still unknown.

The composition (a) contains a polysaccharide as the primary component. Preferably, the composition (a) contains a polysaccharide whose primary constituents are arabinose, mannose, and glucose, and a small amount of nucleic acid. The polysaccharide preferably has a molecular weight ranging from $5\times10^2$ to $5\times10^4$ as measured by the gel filtration method. The nucleic acid content of composition (a) is preferably 0.05–0.3 wt. %. The composition may contain 1–5 wt. % of protein. Preferably, the mannose content of the polysaccharide is 10–72 wt. %, the arabinose content 3–30 wt. %, and the glucose content 5–30 wt. %, and particularly preferred are 40–50 wt. % mannose, 15–25 wt. % arabinose, and 5–15 wt. % glucose.

The composition (a) is obtained by purifying a hot-water extract of human-type tubercle bacillus. In more detail, composition (a) is obtained by subjecting cells of human-type tubercle bacillus to extraction with hot water, and the extract is then subjected to protein removal treatment and to treatment for removing polysaccharides having molecular weights of $10^5$ or more. The tubercle bacillus is not particularly limited so long as it is of the human type; particularly preferred is an AOYAMA B strain. Among the aforementioned steps, extraction with hot water is preferably performed with 80–120° C. water. The protein removal treatment is preferably performed by causing proteins to precipitate by use of a protein precipitant such as sulfosalicylic acid, trichloroacetic acid, or phosphotungstic acid; and subsequently collecting the supernatant. The treatment to remove polysaccharides having molecular weights of $10^5$ or more is preferably performed by causing polysaccharides having high molecular weights to precipitate by use of ethanol, methanol, or acetone in a suitable amount; and subsequently collecting the supernatant.

The component (b); a nucleoside-type anti-HIV agent, is not particularly limited. Preferably, there is used as component (b) one or more members selected from among Zidovudine (Azidothymidine, AZT), Didanosine (ddI), Zalcitabin (ddC), Stavudine (d4T) and Lamivudime (3TC). Azidothymidine is particularly preferred.

In the present invention, the composition (a) is preferably administered to a subject in need thereof by injection, particularly preferably subcutaneous injection. The nucleoside-type anti-HIV agent (b) is preferably administered to a subject in need thereof perorally or by injection, depending on the type of the agent. Examples of the forms of the agent for oral administration include granules, tablets, capsules, and liquids.

The dose of the composition (a) is preferably 2–200 μg per day, more preferably 20–100 μg per day, as calculated in terms of the saccharide content of arabinose. The dose of the nucleoside anti-HIV agent (b), which differs in accordance with the type of drug and administration route, is preferably 50–1500 mg per day, more preferably 200–1000 mg per day, in the case of oral administration.

When the composition (a) and the nucleoside-type anti-HIV agent (b) are administered to a subject in need thereof, they are preferably respectively prepared into pharmaceutical compositions suitable for the aforementioned administration routes by incorporating thereto a generally employed, pharmaceutically acceptable carrier. Examples of carriers useful for the preparation of pharmaceutical compositions include vehicles, binders, lubricants, disintegrants, coating agents, emulsifiers, suspensions, solvents, stabilizers, absorption aids, water for injection use, and tonicity agents.

EXAMPLES

The present invention will next be described by way of examples, which should not be construed as limiting the invention thereto.

Referential Example 1
(Preparation of composition (a))

Mycobacterium tuberculosis strain Aoyama B which had been lyophilized and stored at −20° was subjected to seed culture at 37±1° C. in a Sauton-potato medium:[(1)]. The resultant cells were inoculated to a production medium [(2)], and incubated for 5–7 weeks at 37±1° C. The harvested cells were washed with water for injection use, and to the wet cells was added water for injection use in an amount 20 times that of the weight of the wet cells. The mixture was heated at 100° C. for 120 minutes, to thereby obtain an extract. The extract was filtered by use of a 0.45 μm-membrane filter and concentrated under reduced pressure so that the saccharide content (converted to D-arabinose by the phenol-sulfuric acid method) fell within the range of 4.0–6.0 mg/ml, to thereby obtain a concentrate. Subsequently, in order to remove proteins, one (w/v) % sulfosalicylic acid was added to the concentrate. The mixture was allowed to stand for 15–20 minutes at a temperature of not higher than 10° C. Precipitates were removed by centrifugal separation (10° C. or lower temperature, 1,150× G, 10 minutes), to thereby recover the supernatant. The protein concentration of the supernatant was not more than 0.30 mg/ml (Lowry method, calculated as tyrosine). The supernatant was further processed to remove sulfosalicylic acid until the content of sulfosalicylic acid was below the detection limit (10 ppm or less, colorimetric method using ferric chloride solution). The resultant solution was concentrated under reduced pressure so that the saccharide content fell within the range of 1.8–2.2 mg/ml, and the concentrate was combined with sodium chloride (0.9 (w/v) %) and cold ethanol whose volume is the same as that of the concentrate. The mixture was allowed to stand for not less than 40 hours at a temperature of not higher than 10° C., and then the precipitates polysaccharide of high molecular weight region were removed by centrifugal separation (10° C. or lower temperature, 2,040×G, 10 minutes). Subsequently, the supernatant was combined with four times the amount of cold ethanol, and the mixture was allowed to stand for not less than 40 hours at a temperature of not higher than 10 C., to thereby recover precipitates. The precipitates were dissolved in water for injection use and after the saccharide content was adjusted to 1.8–2.2 mg/ml, the solution was subjected to filtration by use of a 0.45 μm membrane filter and to sterilization in an autoclave (121° C., 20 minutes), to thereby prepare a composition (a) solution.

(1) Sauton-potato medium Washed potato slices were soaked in a Sauton medium, followed by sterilization for 15 minutes at 115° C. The resultant material was used as a Sauton-potato medium.

| Sauton Medium | |
|---|---|
| L-asparagine (monohydrate) | 4.0 g |
| Citric acid (monohydrate) | 2.0 g |
| Magnesum sulfate (heptahydrate) | 0.5 g |
| Potassium monohydrogenphosphate (anhydrate) | 0.5 g |
| Ammonium iron citrate | 0.05 g |
| Glycerol | 60 ml |

The above ingredients were dissolved in water to make a total volume of 1,000 ml. By use of sodium hydroxide solution, pH was adjusted to 7.0–7.3.

(2) Production medium

| | |
|---|---|
| L-asparagine (monohydrate) | 4.0 g |
| Citric acid (monohydrate) | 2.0 g |
| Magnesium sulfate (heptahydrate) | 0.5 g |
| Potassium monohydrogenphosphate (anhydrate) | 0.5 g |
| Ammonium iron citrate | 0.05 g |
| Glycerol | 60 ml |

The above ingredients were dissolved in water to make a total volume of 1,000 ml, followed by sterilization in an autoclave (121° C., 20 minutes). By use of sodium hydroxide solution, pH was adjusted to 7.0–7.3.

The physicochemical properties of the composition (a) solution were as follows.

| | |
|---|---|
| (1) Appearance: | Pale yellow clear liquid |
| (2) pH: | 4.50–5.30 |
| (3) Protein content: | 3.5 wt % (as an amino acid) in a freeze-dried product |
| (4) Nucleic acid content: | 0.1 wt % in a freeze-dried product |
| (5) Constituent monosaccharides of polysaccharide: | Mannose 43.4 wt %, Arabinose 18.2 wt. %, and Glucose 10.4 wt. %. |

Methods for determining the constituent monosaccharides of polysaccharide: The polysaccharide was hydrolyzed with 2N trifluoroacetic acid for two hours at 100° C., and then subjected to liquid chromatography making use of 2-cyanoacetamide fluoroscein derivative (S. Honda, et al., Anal. Chem., 52, 1079 (1980)).

Test Example

In accordance with the method described in Antimicrobial Agents and Chemotherapy, Apr. 1990, p.605–609, culture supernatant (0.1 ml) of SC-1 cells infected with LP-BM5 murine leukemia virus was intraperitoneally administered to each of a group of male C57BL/6 mice, to thereby create murine AIDS (MAIDS) mice. AZT and/or composition (a) (a solution obtained in Referential Example 1) were/was administered to the MAIDS mice from the day following the viral infection. AZT was orally administered to each mouse at a dose of 10 mg/kg/day every four days. In the case of composition (a), the solution obtained in Referential Example 1 was intraperitoneally administered to each mouse at a dose of 10 mg/kg/day (calculated as the saccharide content) every two days.

After administration of AZT and/or composition(a), the MAIDS mice were bred for 145 days under observation. The survival rate was determined, and the therapeutic effects of AZT and composition (a) were evaluated. The survival rates after 130 days are summarized in Table 1 and the chronological changes of the survival rates are shown in FIG. 1.

TABLE 1

| Group | No. of mice | Alive | Dead | Survival rate (%) |
| --- | --- | --- | --- | --- |
| Control | 22 | 8 | 14 | 36 |
| Comp. (a) | 10 | 3 | 7 | 30 |
| AZT | 10 | 6 | 4 | 60 |
| Comp. (a) + AZT | 10 | 8 | 2 | 80 |

Statistical significance between the control group and the treated group in a survival rate was evaluated at day 130 after the viral infection.
*: p = 0.027, compared with control (Fisher's exact method).

As shown in Table 1 and FIG. 1, mortality of MAIDS mice administered with AZT and composition (a) was clearly improved as compared with that of MAIDS mice administered with AZT alone.

As described above, the therapeutic method of the present invention provides remarkably improved therapeutic effect on AIDS patients as compared with the case in which a nucleoside-type anti-HIV agent alone is administered.

What is claimed is:

1. A method of treating AIDS, comprising administering to an HIV-infected patient an effective amount of
   (a) a composition comprising a polysaccharide produced by a hot aqueous solvent extraction of tubercle bacillus, wherein the polysaccharide is comprised of arabinose, mannose and glucose residues, and
   (b) a nucleoside anti-HIV agent.

2. The method of claim 1, wherein the composition further comprises nucleic acid produced by the hot aqueous solvent extraction of tubercle bacillus.

3. The method of claim 1, wherein the polysaccharide has a molecular weight of about $5 \times 10^2 - 5 \times 10^4$, as determined by gel filtration.

4. The method of claim 1, wherein the tubercle bacillus is a human tubercle bacillus.

5. The method of claim 4, wherein the human tubercle bacillus is an Aoyama B strain.

6. The method of claim 1, wherein the nucleoside anti-HIV agent is selected from the group consisting of Zidovudine (Azidothymidine, AZT), Zalcitabin (ddC), Stavudine (d4T), Didanosine (ddI) and Lamivudime (3TC).

7. The method of claim 1, wherein the hot aqueous solvent extraction is conducted at a temperature of about 80° C. to 120° C.

8. The method of claim 1, wherein the composition further comprises about 1 to 5 wt. % of protein.

9. The method of claim 1, wherein the polysaccharide is comprised of 10–72 wt. % mannose, 3–30 wt. % of arabinose and 5–30% wt. % of glucose.

10. The method of claim 1, wherein the polysaccharide is comprised of 40–50 wt. % mannose, 15–25 wt. % of arabinose and 5–15% wt. % of glucose.

11. The method of claim 1, wherein the aqueous solvent is fresh water, saline, sea water, or sodium hydroxide solution.

12. The method of claim 1, wherein the aqueous solvent is fresh water.

13. The method of claim 1, wherein (a) and (b) are administered separately.

14. A composition, comprising:
   (a) a composition comprising a polysaccharide produced by a hot aqueous solvent extraction of tubercle bacillus, wherein the polysaccharide is comprised of arabinose, mannose and glucose residues, and
   (b) a nucleoside anti-HIV agent.

15. The composition of claim 14, wherein the composition further comprises nucleic acid produced by the hot aqueous solvent extraction of tubercle bacillus.

16. The composition of claim 14, wherein the polysaccharide has a molecular weight of about $5 \times 10^2 - 5 \times 10^4$, as determined by gel filtration.

17. The composition of claim 14, wherein the tubercle bacillus is a human tubercle bacillus.

18. The composition of claim 17, wherein the human tubercle bacillus is an Aoyama B strain.

19. The composition of claim 14, wherein the nucleoside anti-HIV agent is selected from the group consisting of Zidovudine (Azidothymidine, AZT), Zalcitabin (ddC), Stavudine (d4T), Didanosine (ddI) and Lamivudime (3TC).

* * * * *